United States Patent
Hollstein

(10) Patent No.: US 9,933,391 B2
(45) Date of Patent: Apr. 3, 2018

(54) ULTRASOUND-BASED GAS BUBBLE AND/OR SOLID DETECTOR, DIALYSIS APPARATUS AND METHOD FOR SUCH DETECTOR

(71) Applicant: B. BRAUN AVITUM AG, Melsungen (DE)

(72) Inventor: Rolf Hollstein, Alheim-Heinebach (DE)

(73) Assignee: B. BRAUN AVITUM AG, Melsungen (DE)

(*) Notice: Subject to any disclaimer, the term of this patent is extended or adjusted under 35 U.S.C. 154(b) by 94 days.

(21) Appl. No.: 15/070,567

(22) Filed: Mar. 15, 2016

(65) Prior Publication Data
US 2016/0274061 A1 Sep. 22, 2016

(30) Foreign Application Priority Data
Mar. 17, 2015 (DE) .................. 10 2015 103 938

(51) Int. Cl.
| | |
|---|---|
| *G01N 29/02* | (2006.01) |
| *G01N 29/032* | (2006.01) |
| *A61M 5/36* | (2006.01) |
| *A61M 5/168* | (2006.01) |
| *A61M 1/36* | (2006.01) |

(52) U.S. Cl.
CPC .......... *G01N 29/02* (2013.01); *A61M 1/3626* (2013.01); *A61M 5/16831* (2013.01); *A61M 5/365* (2013.01); *G01N 29/032* (2013.01); *A61M 2205/3375* (2013.01); *A61M 2205/702* (2013.01); *G01N 2291/015* (2013.01); *G01N 2291/02433* (2013.01); *G01N 2291/048* (2013.01); *G01N 2291/102* (2013.01)

(58) Field of Classification Search
CPC ........ A61M 1/3626; A61M 2205/3375; A61M 2205/702; A61M 5/16831; A61M 5/365; G01N 2291/015; G01N 2291/02433; G01N 2291/048; G01N 2291/102; G01N 29/02; G01N 29/032
See application file for complete search history.

(56) References Cited

U.S. PATENT DOCUMENTS

| | | | |
|---|---|---|---|
| 5,191,795 | A | 3/1993 | Fellingham et al. |
| 6,212,936 | B1 | 4/2001 | Melsburger |
| (Continued) | | | |

FOREIGN PATENT DOCUMENTS

| | | |
|---|---|---|
| DE | 197 38 146 | 3/1999 |
| DE | 10 2005 025 500 | 10/2006 |
| (Continued) | | |

OTHER PUBLICATIONS

Wells, P. N. T. "The medical applications of ultrasonics." Reports on Progress in Physics 33.1 (1970): 45.*

(Continued)

*Primary Examiner* — Lisa Caputo
*Assistant Examiner* — Punam Roy
(74) *Attorney, Agent, or Firm* — RatnerPrestia

(57) ABSTRACT

An ultrasound-based air bubble and/or solid detector comprising an ultrasonic transmitter for transmitting ultrasound through a medium to be examined, wherein the ultrasound is adapted to be received by an ultrasonic receiver. Energy input of the ultrasound into a medium to be monitored may be limited and/or monitored and/or adapted.

12 Claims, 3 Drawing Sheets

(56) References Cited

U.S. PATENT DOCUMENTS

| | | |
|---|---|---|
| 6,324,901 B1 | 12/2001 | Flueh et al. |
| 8,091,407 B2 | 1/2012 | Schneider et al. |
| 8,430,834 B2 | 4/2013 | Kopperschmidt |
| 2012/0285870 A1 | 11/2012 | Wright et al. |

FOREIGN PATENT DOCUMENTS

| | | |
|---|---|---|
| DE | 10 2006 045 452 | 4/2008 |
| EP | 0 416 911 | 3/1996 |
| EP | 0 597 817 | 7/2003 |

OTHER PUBLICATIONS

German Search Report for DE 10 2015 103 938.9 dated Nov. 30, 2015, with translation.
European Search Report for EP 16 160 162.0 dated Jul. 16, 2016, with translation.

* cited by examiner

ULTRASOUND-BASED GAS BUBBLE AND/OR SOLID DETECTOR, DIALYSIS APPARATUS AND METHOD FOR SUCH DETECTOR

CROSS REFERENCE TO RELATED APPLICATIONS

This application claims priority to German application DE 10 2015 103 938.9 filed Mar. 17, 2015, the contents of such application being incorporated by reference herein.

FIELD OF THE INVENTION

The invention relates to an ultrasound-based gas bubble and/or solid detector for monitoring a medium. Furthermore, the invention relates to a dialysis apparatus comprising such detector and a method comprising such detector.

BACKGROUND OF THE INVENTION

In dialysis apparatuses usually ultrasound-based detectors (hereinafter referred to as detector) are used to protect patients against dangerous air embolisms. For this purpose, a part of an extracorporeal blood circuit to be monitored may be guided in the form of a blood hose through an ultrasonic path of the detectors. For this, a detector includes a piezo element that transmits an ultrasonic (US) pulse or US waves through the blood hose by electric excitation to its resonance frequency. The further detector in the form of a piezo element may convert said US pulse into an electric signal. This signal may be compared to a reference voltage and evaluated by a comparator. On the output side of the comparator a signal is available which informs about whether "air" or "no air" (i.e. fluid or blood only) is provided in the ultrasonic path.

DESCRIPTION OF THE RELATED ART

According to the publication "Magnetic resonance imaging methods in medicine. From technology to medical application." by Prof. Dr. Olaf Doessel, Karlsruhe University, ISBN 3-540-66014-3, US pulses may damage the blood of the patient guided through the blood hose. The damage may especially occur by heat impact and by cavitation. Heat is locally generated proportionally to the sound intensity absorbed by the blood. Cavitation is an effect in which in a vacuum phase of a US pulse gas bubbles which then collapse in a pressure phase are formed in the tissue.

The publication DE 197 381 46 B4 discloses an ultrasonic transducer that is operated on or in the vicinity of a resonance frequency so as to generate a strong output signal at the ultrasonic transducer. During use of said ultrasonic transducer the afore-described damages in the blood may occur.

SUMMARY OF THE INVENTION

In contrast, an object underlying the invention is to provide an ultrasound-based gas bubble and/or solid detector which can be safely used with little effort in terms of devices. Another object underlying the invention is to provide a dialysis apparatus comprising an ultrasound-based air bubble and/or solid detector which has a simple design and can be safely employed. Moreover, it is an object of the invention to provide a method for a detector by which a medium to be monitored can be safely monitored in a simple manner in terms of devices.

The object regarding the ultrasound-based air bubble and/or solid detector is achieved according to the features of the independent claim, the object regarding the dialysis apparatus is achieved according to the features of the apparatus claims and the object regarding the method is achieved according to the features of the method claims.

In accordance with an aspect of the invention, an ultrasound based air bubbles and/or solids detector (hereinafter referred to as detector), especially an ultrasonic air bubbles detection system or device, for detecting air in a medium, especially in blood, is provided. The detector has an ultrasonic (US) transmitter for transmitting ultrasound via or through the medium to an ultrasonic (US) receiver of the detector. Advantageously the energy input into the medium is monitored and/or limited on the basis of the ultrasound, for which purpose a monitoring and/or limiting means adapted thereto is provided.

This solution has the advantage that an excessive energy input into the medium can be detected and prevented. When the detector is used, for example, for dialysis, damaging of the blood by excessive energy input and e.g. hemolysis resulting herefrom can be prevented by the detector according to aspects of the invention. Thus the medium to be monitored and/or to be examined can be protected against excessive energies and, respectively, against an excessive energy input. The energy input to the medium to be monitored is thus limited to a tolerable degree. Another advantage of monitoring the energy input is that with the knowledge of the input energy and by means of the ultrasound received by the US receiver (amplitude and time signal course) the nature of an object or of a foreign medium in the medium to be monitored can be concluded. When, for example, a known medium (air) is concerned in the medium to be monitored, even the geometry (dimension, volume) can be concluded by means of the received ultrasound.

In terms of devices, the energy input is monitored simply by monitoring an ultrasound generation. The ultrasound generation, in turn, takes place by a control signal. The US transmitter may be controlled via a control unit (microprocessor, microcontroller, μC) by the control signal. For monitoring the energy input simply the control signal of the control unit then can be tapped. Thus, by monitoring the ultrasound generation the energy input can be checked in a way simple in terms of devices, which does not require any additional sensors, for example.

The tapped control signal preferably can be monitored by a second control unit (microprocessor, microcontroller, μC) which in this case constitutes the monitoring and/or limiting means. In this way, advantageously the monitoring is not left to the first control unit but is carried out by a second additional control unit, thus causing the safety of the system to be increased, especially when the first control unit is defective. The second control unit can compare the control signal to a target control signal, for instance, and thus carry out pattern matching. It is imaginable that the second control unit restricts the energy input by appropriate measures, if required.

Of advantage, each of the US transmitter (transducer) and the US receiver (transducer) is formed by at least one piezo element. For emitting the ultrasound voltage of a voltage means or energy of an energy storage device then may be applied to the US transmitter. The voltage means is an inductor arranged electrically in parallel to the US transmitter, for example. Alternatively or additionally, it is possible that the voltage means is a voltage doubler circuit (cascade circuit). The voltage means may also include circuits which follow the principle of switching controllers.

Preferably, a burst interval of the control signal is monitored. It constitutes a time interval between starting times of two successive charging operations of the voltage means. When the burst interval is reduced, an increase in the energy input in the medium can be concluded. The burst interval is compared to a target burst interval e.g. for monitoring.

As an alternative or in addition to the burst interval, a charging time of the voltage means predetermined by the control signal or the energy in the energy storage device may be monitored. When the charging time of the voltage means is increased, higher energy input can be assumed. A change can be determined especially when a target charging time is considered.

Alternatively or additionally it is imaginable to monitor for each burst interval a number of stimuli (rectangular signals, pulses) output by the US transmitter which are predetermined especially by the control signal. Said stimuli then can be compared to a target number. If the number of stimuli increases, higher energy input has to be assumed.

Moreover, it may be provided to monitor, alternatively or additionally, an ultrasonic (US) excitation frequency of the US transmitter which may be predetermined by the control signal. Said frequency then is compared to a target US excitation frequency, for example. Higher energy input may be caused, for instance, by varying the US excitation frequency.

As an alternative or in addition, a period of the control signal can be monitored.

When a variation of the burst interval and/or of the charging time and/or of the number of stimuli and/or of the US excitation frequency and/or of the period is/are determined, an error signal can be output, especially by the second control unit. The mentioned variations of the respective parameters can occur by temporary or permanent erroneous function of the first control unit (software and/or hardware errors).

In another configuration of the invention, in the case of defective energy input one measure or plural measures is/are initiated for limiting or stopping the energy input. These measures preferably may be initiated by the second control unit such as stopping the energy supply to the US transmitter, stopping of pumps and/or closing of valves.

For example, the measures in total are also hardware measures in that the defective energy input is limited by one component or plural components (electronics components, hardware components). It is further possible to provide the configuration (dimensioning and, respectively, selection) of inductivity by an appropriate saturation current as a hardware measure. Alternatively or additionally, Z diodes may be provided for voltage restriction. It is furthermore alternatively or additionally imaginable to provide an adaptation or a mismatch of impedances during operation of the piezo elements.

In a further configuration of the invention, the ultrasound received by the US receiver may be convertible to an electric received signal and may be compared to a reference value (reference voltage, reference signal, alarm threshold) by a comparing unit (comparator). Depending on a result of this comparison, an output signal indicating "air" or "no air" for example during use of the detector in a dialysis apparatus is output by the comparing unit.

The voltage means may be connectable to a voltage source and to ground for forming a power circuit. The power circuit may be adapted to be opened and closed by switch control, wherein it is controlled in response to the control signal.

Preferably, a second reference value (test threshold) is provided in addition to the first reference value (alarm threshold). The second reference value then can be used instead of the first reference value especially cyclically and for a predetermined, comparatively short, period of time. Thus the first and second reference values are provided at the input of the comparing unit. By the short-term comparison of the second reference value on the one hand a statement about the functioning of the circuit of the detector can be made and, on the other hand, a statement about coupling the medium which is guided, for example, as fluid in a hose to the detector can be made. If the detector functioned error-free, on the output side of the comparator preferably e.g. "air" would be signalized with the second reference value. Unless this is the case, either a defective circuit may be provided or else the coupling between the medium (for example the fluid guided in the hose) and the US transmitter and/or US receiver may be within inadmissible ranges. For example, an inadmissibly good coupling or even an acoustic short-circuit is possible, which in each case results in falsification of the ultrasound between the US transmitter and the US receiver. This is caused, e.g., by fluid penetrated between the US sensor, the hose and the US receiver. However, also cases from practice are known in which a user of the detector introduces a so called ultrasonic gel to the path of the US sensor, the hose and the US receiver so as to eliminate alleged false alarms. In these cases, too, sensitivity of the US sensor and of the US receiver is reduced, which then can be detected by the described method. The safety system including the reference values in combination with the monitoring of the energy input thus results in a detector which can be used in an extremely safe manner.

By means of the evaluation of the received signal (time, amplitude) statements about the nature of a medium (geometry) within the medium to be monitored can be made. By means of the comparison of the received signal (time, amplitude) to the different reference values statements about the correct function of the sensor as well as the proper coupling between the sensor and the medium to be monitored (hose and fluid) can be realized, as already explained in the foregoing. The prerequisite for the safe derivation of the received signal is the safe knowledge of the ultrasound (transmission signal). This can be achieved by realizing the monitoring of the ultrasound described in the beginning.

In accordance with the invention, a dialysis apparatus or an infusion apparatus comprising a detector according to any one of the preceding aspects is provided. Between the US transmitter and the US receiver a flow path (hose) through which the medium (blood or infusion fluid) can flow may be arranged. The use of the detector results in high safety for a patient connected to the dialysis apparatus, because any damage of the blood due to high energy input into the blood is prevented.

The first control unit of the dialysis apparatus may be provided for regulating and controlling components of the dialysis apparatus and of the detector. The second control unit (supervisor) then can initiate measures to protect the patient and can additionally monitor and/or restrict the energy input into the medium. In this way a defect or malfunction of the first control unit is safely detected by the second control unit and consequently appropriate protective measures can be initiated.

In the case of defective energy input, in the dialysis apparatus for example one pump or more pumps may be stopped and/or one hose shut-off clamp or plural hose shut-off clamps is/are closed.

An ultrasound-based method for an air bubble and/or solid detector according to aspects of the invention in accordance with any one of the preceding aspects comprises the following steps of:
transmitting ultrasound by an ultrasonic (US) transmitter via a medium to be monitored to an ultrasonic (US) receiver of the air bubble and/or solid detector and
monitoring and/or limiting energy input into the medium on the basis of ultrasound. In this way, when ultrasounds are applied to blood the latter is prevented from being damaged.

Other advantageous developments of the invention are the subject matter of further subclaims.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
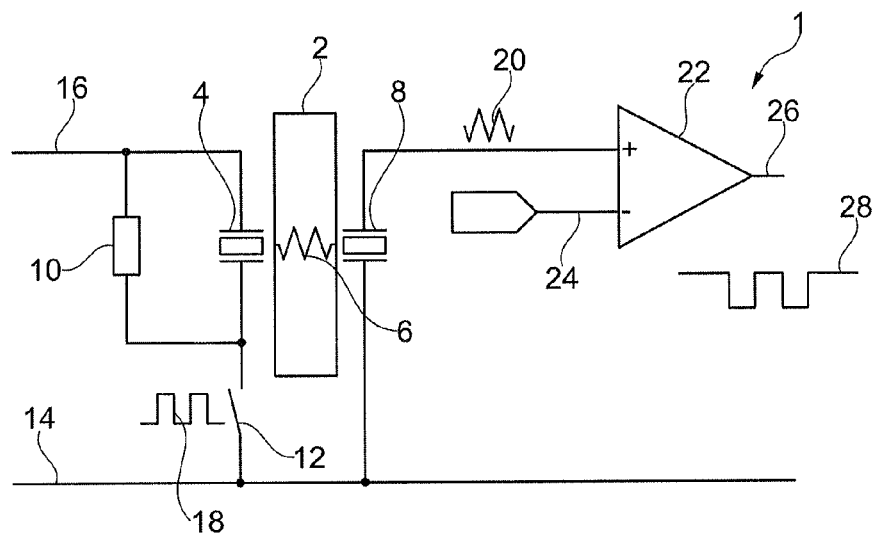
FIG. 1 shows in a schematic representation a detector according to aspects of the invention.

According to FIG. 1, an ultrasound-based gas bubble or air bubble detector 1 (hereinafter referred to as detector) is provided for the detection of air in a medium in the form of blood of a dialysis patient, the blood flowing through a hose 2. For this purpose, the detector 1 includes an ultrasonic (US) transmitter 4 in the form of a piezo element for transmitting ultrasound 6 through the hose 2. The ultrasound 6 can be received by an ultrasonic (US) receiver 8. The US transmitter 4 and the US receiver 8 thus form an ultrasonic path. For emitting an ultrasound voltage is applied to the US transmitter 4 via inductor 10 arranged electrically in parallel to the US transmitter 4. The US transmitter 4 and the inductor 10 are connectable to ground 14 via a switch 12. Moreover, they are connected to a voltage source 16. A self-induction voltage of the inductor 10 which is formed upon opening the switch 12 serves for making available the voltage required for the US transmitter 4. Then the US transmitter 4 is controlled via a control signal 18. The control signal 18 is provided by a control unit not shown in FIG. 1. The ultrasound 6 is received by the US receiver 8 and is converted to an electric received signal 20. The latter then is compared to a reference voltage 24 and evaluated by a comparing unit 22 (comparator). An output signal 28 which informs about whether "air" or "no air" (i.e. fluid only) is provided in the ultrasonic path is provided at an output 26 of the comparing unit 22.

Figure 2:
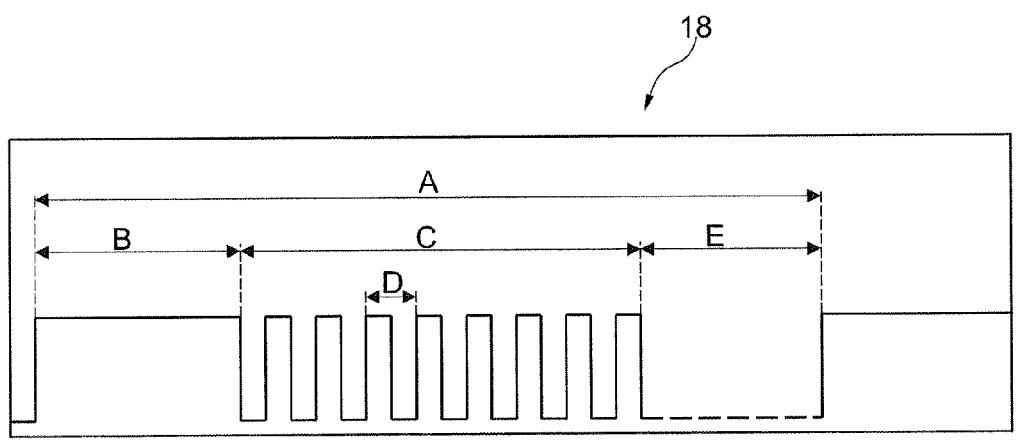
FIG. 2 shows in a schematic representation a control signal for an ultrasonic transmitter of the ultrasonic detector.

In FIG. 2 the control signal 18 is shown which is monitored in the case of the detector 1 according to aspects of the invention of FIG. 1 so as to monitor and/or to limit in turn energy input into the blood guided within the hose 2 on the basis of the ultrasound 6. According to FIG. 2, the control signal 18 has a burst interval A amounting to 50 and 900 µs, for example. A frequency of the burst interval A amounts to, e.g., 1 to 15 kHz. A charging time B of the inductor 10 of FIG. 1 amounts to 5 to 20 µs, for example. Then the burst interval A is the distance of two starting times of successive charging times B.

After expiry of a charging time B, upon the control signal 18 a number C of stimuli having a US excitation frequency D of the US transmitter 4 of e.g. 1 to 5 MHz are carried out. For example eight stimuli (C=8) are provided. In the case of a US excitation frequency of 2 MHz, for example, an interval between two stimuli amounts to 500 ns. After the number C of ultrasonic stimuli a break E is provided, until the charging time B starts again. This break amounts, for example, to 300 to 500 µs (e.g. 481 µs).

For monitoring the energy input now the burst interval A and/or the charging time B and/or the US excitation frequency D and/or the number C of the stimuli are monitored. If, in the case of error, the burst interval A is reduced, it has to be assumed that a higher energy input into the hose 2 comprising the blood takes place. Equally, a higher energy input has to be expected, when the charging time B of the inductor 10 increases. Moreover, a higher energy input into the blood has to be assumed, if the afore-determined number C of the stimuli increases in a possible case of error. Higher energy input into the blood may also be caused by a change of the US excitation frequency D. The listed changes of the respective parameters may occur on the software side or the hardware side, for example, by temporary or permanent malfunction of the microprocessors used for the control unit that generate the control signal.

The control signal 18 of FIG. 2 is available at the switch 12 and from there may be transmitted to a monitoring control unit. The knowledge of the energy input further results in the fact that by means of the received signal 20 (amplitude and time signal course) the nature of an object or foreign medium within the medium to be monitored, blood in this case, may be concluded. If a known medium such as in this case the air to be monitored is concerned, the geometry (dimensions, volume) can be concluded by means of the received signal 20.

Figure 3:
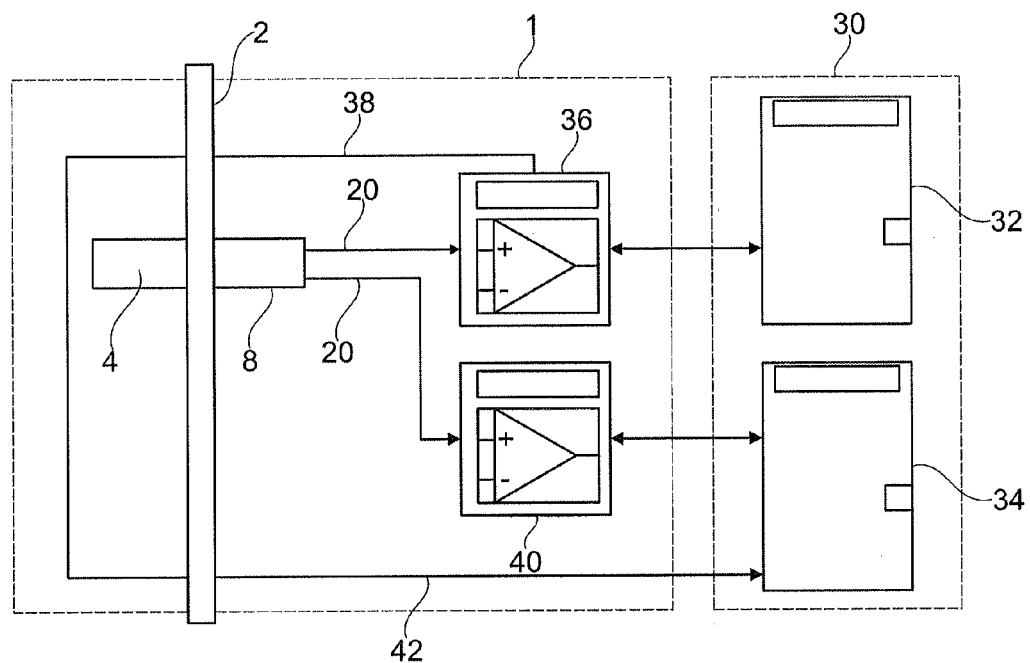
FIG. 3 shows in a schematic representation a dialysis apparatus comprising a detector.

According to FIG. 3, in addition to the detector 1 a dialysis apparatus 30 including the detector 1 is schematically shown. The dialysis apparatus 30 includes a first control unit 32 and a second control unit 34 (supervisor). The first control unit 32 serves for regulating and controlling components of the dialysis apparatus 30 and thus also of the detector 1. The second control unit 34 especially serves for monitoring the dialysis apparatus 30 so as to protect a patient making use of the dialysis apparatus 30.

The first control unit 32 together with the microprocessor 36 controls the US transmitter 4 transmitting the ultrasound via the hose 2 to the US receiver 8. In accordance with FIG. 3, the received signal 20 is forwarded to the microprocessor 36 and to a microprocessor 40 connected to the second control unit 34. For monitoring the control signal 18 which serves for controlling the US transmitter 4 via the signal path 38, the control signal 18 is tapped by the US transmitter 4 via a signal path 42 and is supplied to a passage of the second control unit 34 of the dialysis apparatus 30. Then the parameters A through D to be monitored are checked via said passage, see FIG. 2. If any deviation from target parameters is determined by the second control unit 34 in the monitoring passage, said control unit may initiate measures for preventing, stopping or limiting damage of the blood within the hose 2. The measures are, for example, stopping of one or more pumps and/or closing of one or more hose shut-off clamps.

Figure 4:
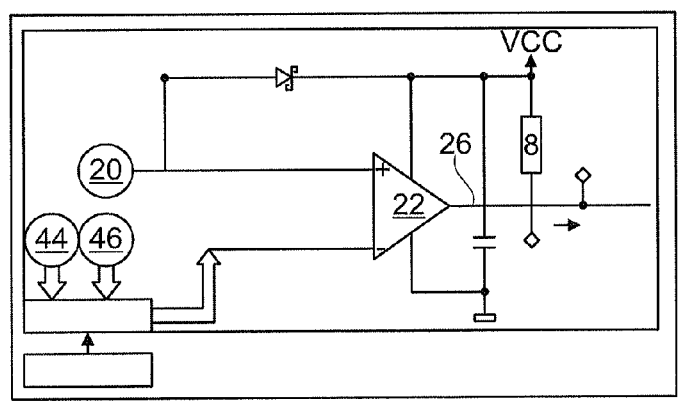
FIG. 4 shows in a schematic representation a comparing unit of the detector for comparing a received signal to a target value.

According to FIG. 4, a method for evaluating the received signal 20 may be combined with the monitoring of the sequence of the control signal 28 of FIG. 1. Said method serves for detecting errors of the US transmitter 4 or the US receiver 8 and for detecting changes of a coupling in the sensor path. In accordance with FIG. 4, the received signal 20 is compared to a reference value 44 which can be referred to as alarm threshold (AS) by the comparing unit 22 or another comparing unit. The comparing unit 22 then indicates at its output 26 "air" or "no air" depending on the received signal 20, as already explained before. If it is now cyclically changed for a short time from the first reference value 44 to a second reference value 46 serving as test threshold (TS) at the input of the comparing unit 22, the received signal 20 is compared to the second reference value 46. Hereby, on the one hand, a statement can be made on the functioning of the circuit illustrated in FIG. 1 and, on the other hand, statements can be made on the coupling between the hose 2 and the US transmitter 4 and, respectively, the US receiver 8. Unless "air" is signalized at the output 26 as expected, when the second reference value 46 is used, either a defective circuit may be provided or else the coupling between the hose 2 and the US transmitter 4 and/or the US receiver 8 may be within inadmissible ranges.

Figure 5:
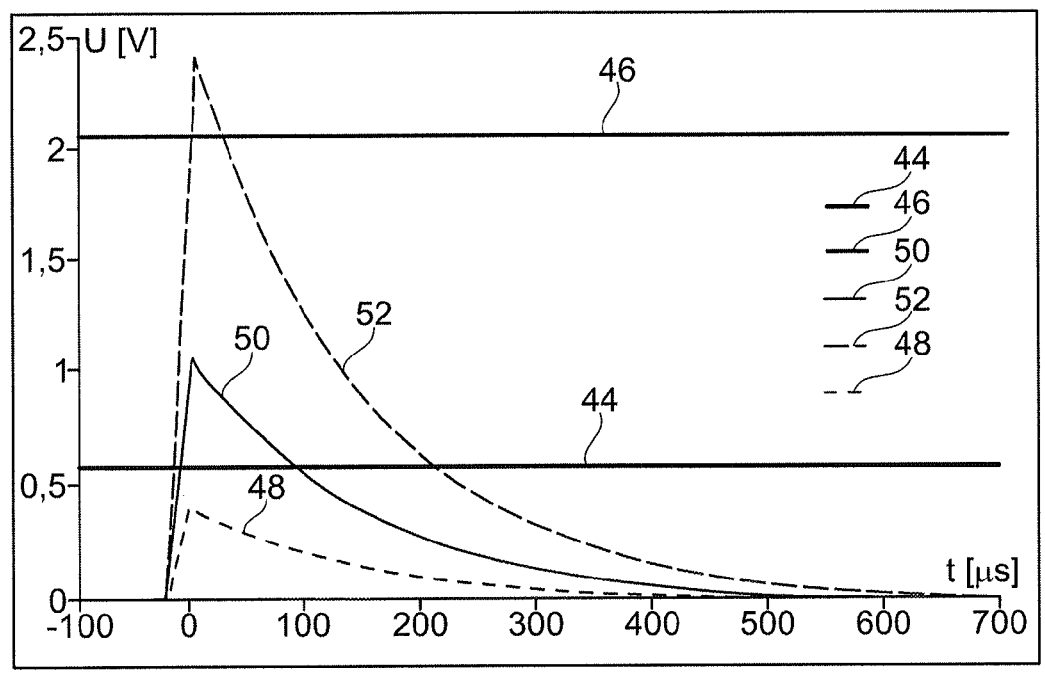
FIG. 5 shows in several curves input parameters for the comparing unit from FIG. 4

According to FIG. 5, by way of plural curves a comparison to the first reference value 44 and to the second reference value 46 is shown. The diagram illustrated in FIG. 5 includes an ordinate indicating a voltage in V and an abscissa indicating a time in μs. In this case the voltage ranges from 0 to 2.5 V and the time ranges from −100 to 700 μs. The first reference value 44 has a voltage ranging from 0.5 to 1 V and the second reference value 46 has a voltage lying between 2 and 2.5 V, with a respective reference value 44, 46 being approximately constant. A curve 48 located below the first reference value 44 according to FIG. 5 represents the received signal 20 of FIG. 1 which is resulting during faultless operation when "air" is provided within the hose 2. In this case, a comparison between the first reference value 44 and also the second reference value 46 would result in the fact that "air" is indicated at the output 26 of the comparing unit 22. A curve 50 intersecting the first reference value 44 in FIG. 5 shows the received signal 20, when "no air" is within the hose 2 during faultless operation. In this case "no air" is issued at the output 26. In a comparison with the second reference value 46 "air" would be displayed. Another curve 52 intersecting the second reference value 46 displays the received signal 20 in the case of faulty coupling. When the curve 52 is compared to the first reference value 44, it would be determined that "no air" is provided as the curve 52 also intersects the first reference value 44. If, however, the second reference value 46 is considered, "air" would have to be displayed during faultless operation, as the curves 48, 50 for the faultless received signal 20 are located below the second reference value 46. Since in a case of fault the curve 52 intersects the straight line of the second reference value 46, "no air" is reported, wherefrom a defective operation can be concluded.

Figure 6:
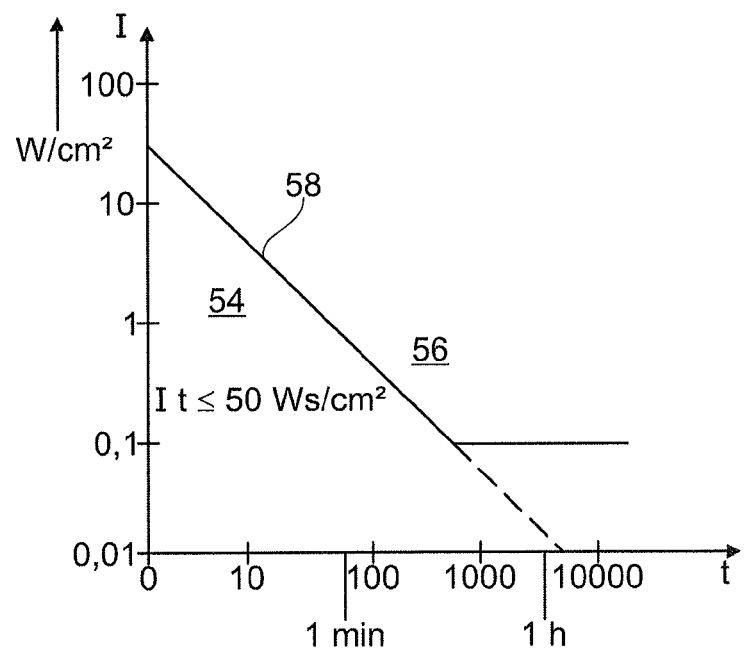
FIG. 6 shows in a diagram the effects of energy input based on ultrasound in the blood of a patient.

In accordance with FIG. 6, a diagram is shown which on the ordinate shows intensity I in W/cm$^2$ of the energy of the ultrasound 6 from FIG. 1 and on the abscissa shows an exposure time t in s of the ultrasound 6. The intensity I is shown logarithmically between 0.01 and 100 and the exposure time is shown logarithmically between 0 and 10 000. Accordingly, a safe range 54 and a possible damaging range 56 are represented which are separated by a curve 58. When the product of intensity and exposure duration (I*t) is within the safety range 54, i.e. the product is ≤50 Ws/cm$^2$, no damage of the blood within the hose 2 of FIG. 1 is provided. If the product is larger, however, and is within the damaging range 56, a damage of the blood may take place, for example by occurrence of hemolysis.

The invention discloses a detector comprising an ultrasonic transmitter for transmitting an ultrasound through a medium to be examined, the ultrasound being adapted to be received by an ultrasonic receiver. Accordingly, energy input of the ultrasound into the medium to be monitored may be limited and/or monitored and/or adapted.

The invention claimed is:

1. An ultrasound-based air bubble and/or solid detector comprising:
   an ultrasonic (US) transmitter configured to generate an ultrasound transmission for transmission through a medium;
   an ultrasonic (US) receiver positioned to receive the ultrasound transmission through the medium from the US transmitter and convert the received ultrasound transmission into an electric received signal;
   a first control unit configured to transmit a control signal to the US transmitter to control the ultrasound transmission of the US transmitter;
   a second control unit configured to:
      monitor the control signal transmitted by the first control unit to determine energy input into the medium by the ultrasound transmission generated by the US transmitter, and
      initiate at least one measure to limit energy input into the medium caused by generation of the ultrasound transmission by the US transmitter if the determined energy input into the medium is excessive; and
   a comparing unit configured to:
      receive the electric received signal from the US receiver,
      compare the electric received signal to a first reference value, and
      generate an output signal indicating a detection result in response to the comparison.

2. The detector of claim 1, wherein each of the US transmitter and the US receiver comprises a piezo element and wherein voltage of a voltage means is applied to the US transmitter for emitting the ultrasound transmission.

3. The detector of claim 2, wherein energy input is limited based on monitoring at least one of:
   a burst interval (A) of the control signal representing a time interval between starting times of two successive charging operations of the voltage means is monitored;
   a charging time of the voltage means;
   a number (C) of stimuli output by the US transmitter per burst interval (A); or
   an ultrasonic excitation frequency (D) of the US transmitter; or
   a period of the control signal.

4. The detector of claim 3, wherein the second control unit outputs an error signal upon at least one of:
   variation of the charging time (B);
   variation of the burst interval (A);
   variation in the number (C) of stimuli;
   variation of the ultrasonic excitation frequency (D); or
   variation of the period.

5. The detector of claim 1, wherein the second control unit is further configured to limit or terminate the energy input if monitored energy input is determined to be faulty.

6. The detector of claim 5, wherein the energy input is limited through hardware.

7. The detector of claim 1, wherein the comparing unit is further configured to compare the electric received signal to a second reference value in addition to the first reference value, and wherein the second reference value is compared to the electric received signal cyclically and for a predetermined time interval.

8. A blood treatment apparatus comprising the detector of claim 1, wherein a flow path through which the medium can flow is arranged between the US transmitter and the US receiver.

9. The blood treatment apparatus according to claim 8, wherein the first control unit is provided for regulating and controlling the blood treatment apparatus and the second control unit is provided for initiating protective measures for a patient and for limiting the energy input into the medium.

10. The blood treatment apparatus of claim 8, wherein the blood treatment apparatus is a dialysis apparatus.

11. The blood treatment apparatus of claim 10, wherein in the case of faulty energy input in the blood treatment apparatus, the second control unit is configured to at least one of stop one or more pumps or close one or more hose shut-off clamps.

12. A method for use with the ultrasound-based air bubble and/or solid detector of claim 1, the method comprising the steps of:
 transmitting, with a first control unit, a control signal to the US transmitter to control the ultrasound transmission of the US transmitter;
 monitoring, with the second control unit, the control signal transmitted by the first control unit to determine energy input into the medium by the ultrasound transmission generated by the US transmitter;
 initiating, with the second control unit, at least one measure to limit energy input into the medium caused by generation of the ultrasound transmission by the US transmitter if the determined energy input into the medium is excessive;
 transmitting the ultrasound transmission with the US transmitter through the medium to the ultrasonic (US) receiver of the detector;
 converting, with the US receiver, the received ultrasound transmission into an electric received signal;
 receiving, with the comparing unit, the electric received signal from the US receiver;
 comparing, with the comparing unit, the electric received signal to a first reference value; and
 generating, with the comparing unit, an output signal indicating a detection result in response to the comparison.

* * * * *